United States Patent
Wang (10) Patent No.: US 6,198,959 B1
(45) Date of Patent: Mar. 6, 2001

(54) CORONARY MAGNETIC RESONANCE ANGIOGRAPHY USING MOTION MATCHED ACQUISITION

(75) Inventor: Yi Wang, New York, NY (US)

(73) Assignee: Cornell Research Foundation Inc., Ithaca, NY (US)

( * ) Notice: Subject to any disclaimer, the term of this patent is extended or adjusted under 35 U.S.C. 154(b) by 0 days.

(21) Appl. No.: 09/246,623

(22) Filed: Feb. 8, 1999

Related U.S. Application Data (60) Provisional application No. 60/079,547, filed on Mar. 27, 1998.

(51) Int. Cl.7 .................................................. A61B 5/055
(52) U.S. Cl. ..................... 600/413; 600/419; 600/509; 324/307; 324/309
(58) Field of Search ................................... 600/413, 419, 600/509, 521; 324/307, 309

(56) References Cited

U.S. PATENT DOCUMENTS

| | | | |
|---|---|---|---|
| 5,277,182 | * | 1/1994 | Koizumi et al. .................. 128/653.3 |
| 5,830,143 | * | 11/1998 | Mistretta et al. ..................... 600/420 |
| 5,897,496 | * | 4/1999 | Watanabe ............................. 600/413 |
| 5,987,348 | * | 12/1999 | Fischer et al. ....................... 600/413 |
| 6,009,341 | * | 12/1999 | Edelman ............................... 600/413 |

OTHER PUBLICATIONS

Navigator–Echo–based Real–Time Respiratory Gating and Triggering for Reduction of Respiration Effects in Three–dimensional Coronary MR Angiography, Radiology 1996; 198:55–60, Wang, et al.

Respiratory Motion of the Heart: Kinematics and the Implications for the Spatial Resolution in Coronary Imaging, MRM 33:713–719 (1995), Wang, et al.

* cited by examiner

Primary Examiner—Francis J. Jaworski
Assistant Examiner—Eleni Mantis Mercader
(74) Attorney, Agent, or Firm—Quarles & Brady LLP

(57) ABSTRACT

Coronary arteries are imaged using a cardiac gated, 3DFT fast gradient recalled echo MRA pulse sequence. A scout scan is performed to measure motion during a cardiac or respiratory cycle and a quiescent period of minimal artery motion is identified. Image data is acquired during a succession of cardiac cycles, and the view order is selected to sample the center of k-space during the quiescent period of each cardiac and or respiratory cycle to reduce motion artifacts.

11 Claims, 9 Drawing Sheets

CORONARY MAGNETIC RESONANCE ANGIOGRAPHY USING MOTION MATCHED ACQUISITION

This application is based in part on U.S. Provisional Application Ser. No. 60/079,547 filed on Mar. 27, 1998.

BACKGROUND OF THE INVENTION

The field of the invention is magnetic resonance angiography ("MRA"), and particularly, studies of the human vasculature using contrast agents which enhance the NMR signals.

Diagnostic studies of the human vasculature have many medical applications. X-ray imaging methods such as digital subtraction angiography ("DSA") have found wide use in the visualization of the cardiovascular system, including the heart and associated blood vessels. One of the advantages of these x-ray techniques is that image data can be acquired at a high rate (i.e. high temporal resolution) so that a sequence of images may be acquired during injection of the contrast agent. Such "dynamic studies" enable one to select the image in which the bolus of contrast agent is flowing through the vasculature of interest. Images showing the circulation of blood in the arteries and veins of the kidneys, the neck and head, the extremities and other organs have immense diagnostic utility. Unfortunately, however, these x-ray methods subject the patient to potentially harmful ionizing radiation and often require the use of an invasive catheter to inject a contrast agent into the vasculature to be imaged. There is also the issue of increased nephro-toxicity and allergic reactions to iodinated contrast agents used in conventional x-ray angiography.

Magnetic resonance angiography (MRA) uses the nuclear magnetic resonance (NMR) phenomenon to produce images of the human vasculature. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles, or "views", in which these gradients vary according to the particular localization method being used. The resulting set of received NMR signals are digitized and processed to reconstruct the image using one of many well known reconstruction techniques.

MR angiography (MRA) has been an active area of research. Two basic techniques have been proposed and evaluated. The first class, time-of-flight (TOF) techniques, consists of methods which use the motion of the blood relative to the surrounding tissue. The most common approach is to exploit the differences in magnetization saturation that exist between flowing blood and stationary tissue. Flowing blood, which is moving through the excited section, is continually refreshed by spins experiencing fewer excitation pulses and is, therefore, less saturated. The result is the desired image contrast between the high-signal, moving blood and the low-signal, stationary tissues.

MRA methods have also been developed that encode motion into the phase of the acquired signal as disclosed in U.S. Pat. No. Re. 32,701. These form the second class of MRA techniques and are known as phase contrast (PC) methods. Currently, most PC MRA techniques acquire two images, with each image having a different sensitivity to the same velocity component. Angiographic images are then obtained by forming either the phase difference or complex difference between the pair of velocity-encoded images.

To enhance the diagnostic capability of MRA a contrast agent such as gadolinium can be injected into the patient prior to the MRA scan. Excellent diagnostic images may be acquired using contrast-enhanced MRA if the data acquisition is properly timed with the bolus passage.

There are a number of techniques for detecting the arrival of the contrast agent in the arteries being imaged. The prevailing thinking is that once the presence of the bolus is detected, the data acquisition should be acquired in a centric view order in which the central region of k-space is acquired first. This approach works well for most vasculature, but this method cannot be used to image the coronary arteries, due to respiratory and cardiac motion.

SUMMARY OF THE INVENTION

The present invention is a method for acquiring MRA data when motion is an important factor in determining image quality. The method consists of two parts. In the first part scout images are acquired of the region of interest during a cardiac cycle to measure movement of the arteries of interest at different cardiac phases. Information acquired from the scout images is used to determine a "quiescent" time interval during mid-diastole when artery motion is minimal, and this is used in the subsequent MRA scan. During the cardiac gated MRA acquisition and after bolus arrival is detected, k-space is sampled during the diastolic portion of the successive cardiac cycles, with the center of k-space being sampled during the quiescent time period and the periphery of k-space being sampled on each side of the quiescent period. Similarly, the acquisition of NMR data may be tailored to other cyclic movements such as that produced by respiration.

A general object of the invention is to reliably image arteries that are subject to motion during the cardiac cycle. By measuring the quiescent period with scout acquisitions and tailoring the subsequent MRA acquisition to the particular patient, the variability in image quality is substantially reduced. It has been discovered that the quiescent period varies considerably between patients and that reliable image quality can be achieved by adapting the MRA acquisition accordingly.

Another object of the invention is to reduce total scan time so that an image can be acquired in a single breath hold. By sampling the periphery of k-space before and after the quiescent period, more views can be acquired during each cardiac cycle without significantly affecting image quality. This is because the peripheral views may be acquired while there is artery motion and the acquisition can be extended over a larger portion of the cardiac cycle without adversely affecting image quality.

Another aspect of the present invention is to tailor the data acquisition to the combined motion produced by the heart and respiration. A scout image is acquired to measure movement of arteries as a function of cardiac phase indicated by a cardiac trigger signal, and a scout image is acquired to measure movement as a function of respiratory phase. A two-dimensional motion phase diagram is produced which is indicative of artery motion during the respiratory gating window and the cardiac acquisition window. This is mapped to segments of k-space to produce a look-up table of views that are to be acquired for any combination of respiratory and cardiac phase.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
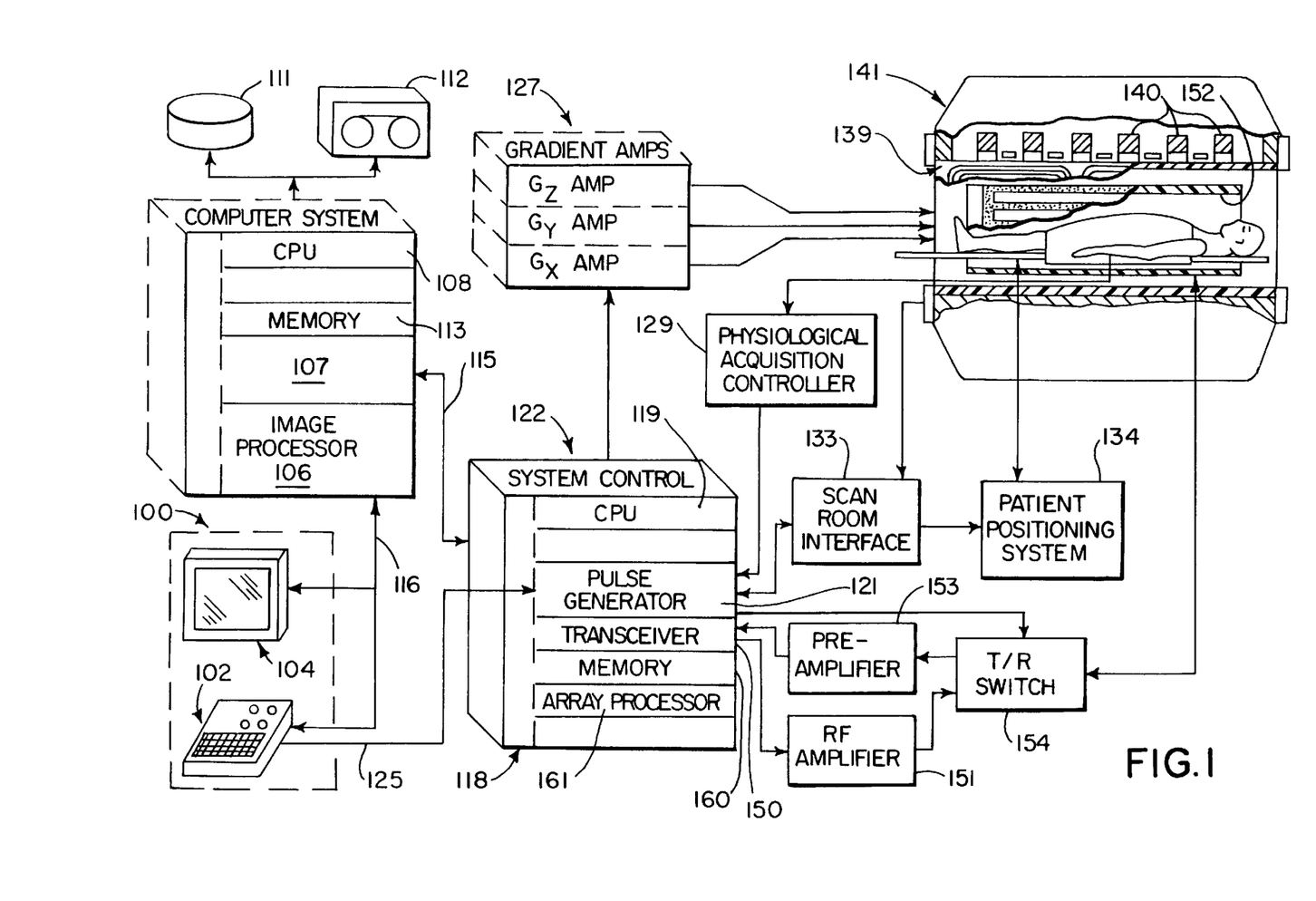
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. To practice the present invention an ECG signal is used to trigger the data acquisition that takes place during a portion of each cardiac cycle. This acquisition sequence is described in more detail below.

The pulse generator module 121 also connects to a scan room interface circuit 133 which receives signals from various sensors associated with the condition of the patient and the magnet system. It is also through the scan room interface circuit 133 that a patient positioning system 134 receives commands from the pulse generator module 121 to move the patient to the sequence of desired positions to perform the scan in accordance with the present invention. The operator can thus control the operation of the patient positioning system 134 through the keyboard and control panel 102.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF local coil to be used during the receive mode.

The NMR signals picked up by the RF local coil are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

Figure 2:
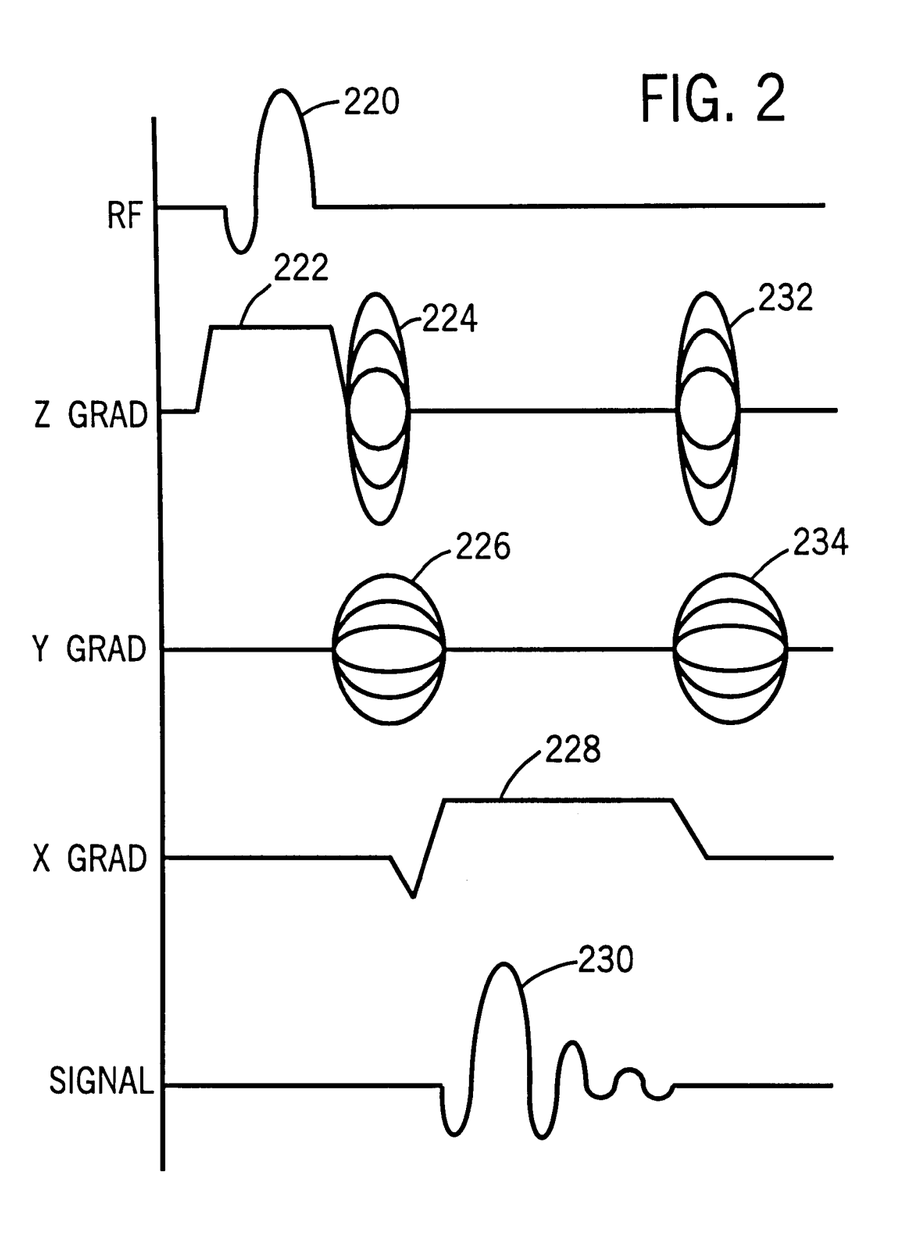
FIG. 2 is a graphic representation of a pulse sequence performed by the MRI system of FIG. 1 to practice a preferred embodiment of the invention.

While many pulse sequences may be used to practice the present invention, in the preferred embodiment a 3D gradient-recalled echo pulse sequence is used to acquire the NMR data. Referring particularly to FIG. 2, an RF excitation pulse 220 having a flip angle of 45° is produced in the presence of a slab select gradient pulse 222 to produce transverse magnetization in the 3D volume of interest as taught in U.S. Pat. No. 4,431,968. This is followed by a phase encoding gradient pulse 224 directed along the logical z axis and a phase encoding gradient pulse 226 directed along the logical y axis. A readout gradient pulse 228 directed along the logical x axis follows and a partial echo (60%) NMR signal 230 is acquired and digitized as described above. After the acquisition, rewinder gradient pulses 232 and 234 are applied to rephase the magnetization before the pulse sequence is repeated as taught in U.S. Pat. No. 4,665,365.

As is well known in the art, the pulse sequence is repeated and the phase encoding pulses 224 and 226 are stepped through a series of values to sample the 3D k-space in the field of view. As will be described in more detail below, it is the order and the extent to which these phase encoding gradients are stepped, and hence the order and shape in which k-space is sampled, which is the subject of the present invention. In the preferred embodiment 16 phase encodings are employed along the z axis and 128 phase encodings are employed along the y axis for a full sampling of k-space. Sampling along the $k_x$ axis is performed by sampling the echo signal 230 in the presence of the readout gradient pulse 228 during each pulse sequence. It will be understood by those skilled in the art that only a partial sampling along the $k_x$ axis may be performed and the missing data is computed using a homodyne reconstruction or by zero filling. This enables the echo time (TE) of the pulse sequence to be shortened to 1 ms and the pulse repetition rate (TR) to be shortened to 5 ms.

Figure 3:
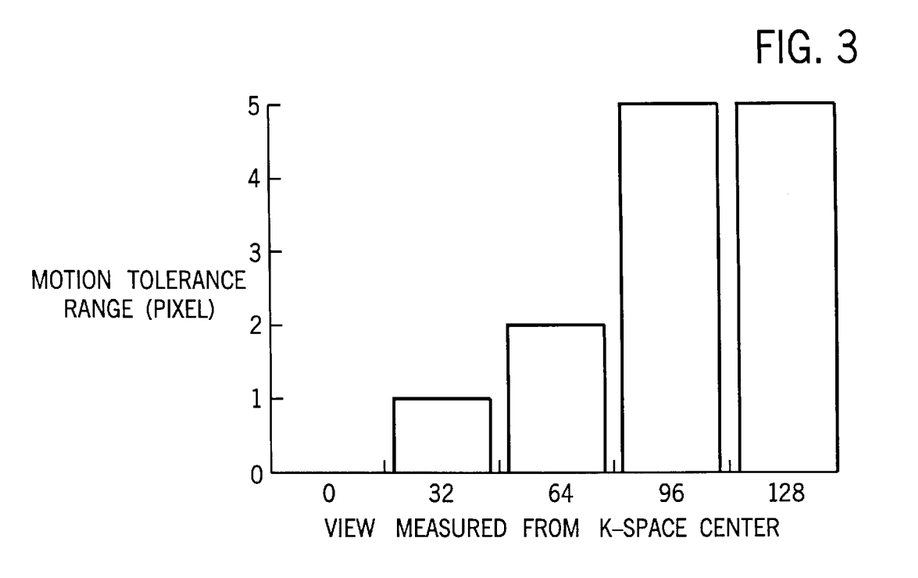
FIG. 3 is a graphic illustration of the motion tolerance of k-space sampling as a function of distance from the center of k-space.

Referring to FIG. 3, the tolerance of MRA images to motion varies accordingly to the location in k-space being sampled during the motion. This phenomena was explored in an experiment in which phase shifts were applied to a group of echoes (8 views) in the raw data of an MR image. The raw k-space data was then Fourier transformed to real image space to demonstrate motion effects. This process was repeated by varying the motion amplitude from 1 to 5 pixels, and by varying the central location of the group of echoes from the center to the edge of k-space. Motion tolerance was judged by 2 radiologists as the point where no diagnostic degradation in image quality occurs. Substantial motion was tolerated at the edge of k-space, but no motion was tolerable at the center of k-space. As will be described below, this observation is used in the data acquisition strategy of the present invention.

Before the MRA scan using the pulse sequence of FIG. 2 is performed, however, a scout scan of the arteries of interest is performed. This scout scan measures the movement of the arteries during a cardiac cycle, and from this information a quiescent period is identified during which the critical, central k-space samples will be acquired according to the present invention.

Figure 4:
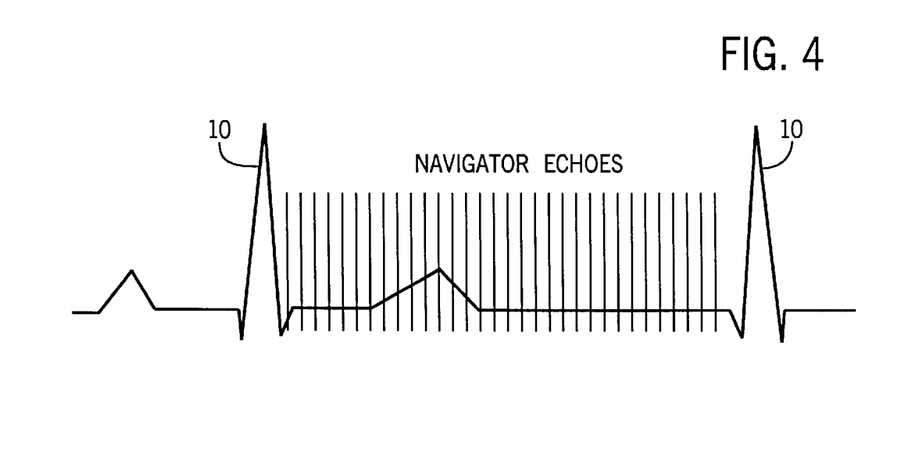
FIG. 4 is a graphic illustration of a scout scan in which navigator echo signals are acquired during a cardiac cycle.
Figure 5:
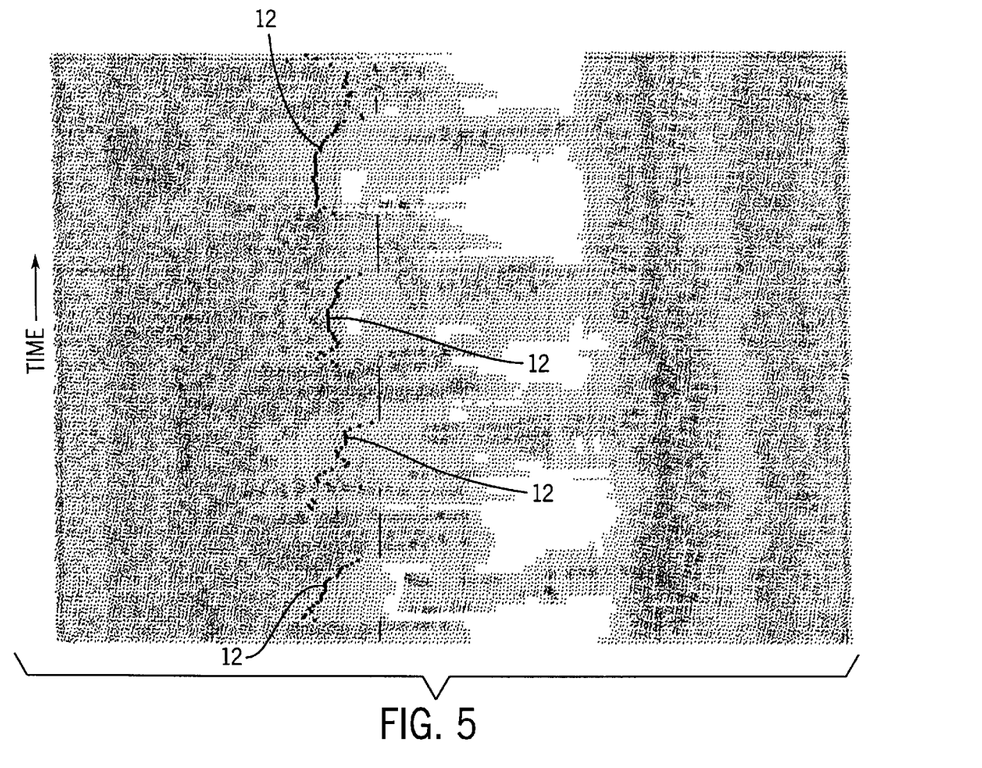
FIG. 5 is a pictorial representation of an image reconstructed from the navigator echo signals acquired in FIG. 4.

Referring to FIG. 4, during a cardiac cycle a navigator echo pulse sequence is repeatedly performed. These navigator sequences are ECG triggered by the QRS complex and are performed continuously during the R—R interval for one cardiac cycle. The preferred navigator pulse sequence is a fast gradient recalled pulse sequence using a flip angle of 15° for the RF excitation pulse. A spiral-gradient, 2D selective RF excitation pulse is employed in which a cylinder of tissue having a 15 mm radius is excited over a 5 ms time period. An effective echo time of 3 ms is achieved and a 20 msec transmit repetition time (TR) is used to acquire 48 NMR navigator echo signals per cardiac cycle. The NMR echo signals are Fourier transformed and combined to form an image data set as depicted in FIG. 5. A least squares algorithm allows reliable detection and tracking of the motion of the ventricular heart cavity wall during diastole as indicated at 12. From this data the movement of the ventricular wall from one 20 msec navigator frame to the next during the entire R—R interval is calculated and a quiescent time period in which movement is below a selected threshold is identified. The size of this quiescent time period has been found to vary from one patient to the next and it typically ranges from 100 msecs to 300 msecs. The location within the R—R interval and duration of the quiescent period is stored for use in the MRA scan to follow.

Figure 6:
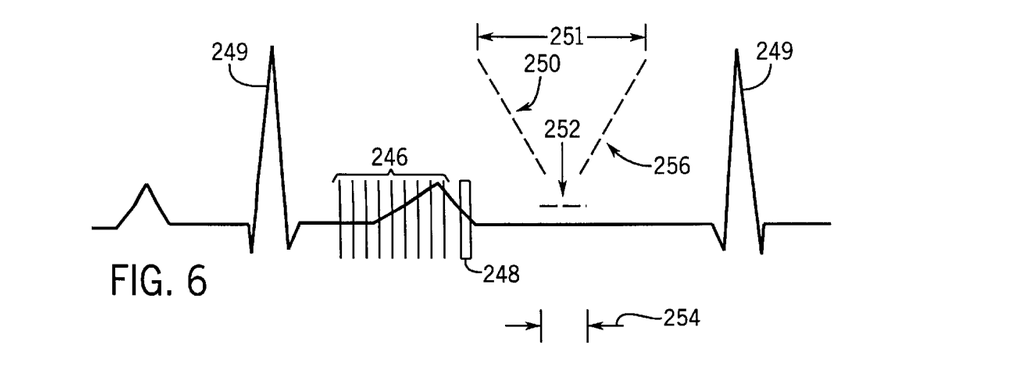
FIG. 6 is a graphic illustration of the data acquisition during one cardiac cycle in a scan according to the present invention.

Referring particularly to FIG. 6, the MRA data acquisition is started after the contrast agent is detected in the arteries being imaged. A set of views are acquired in a succession of cardiac cycles using the 3DFT pulse sequence of FIG. 2. The order in which these views are acquired is an important aspect of the present invention and is illustrated for one cardiac cycle in FIG. 6. Saturation pulses in the form of spatially selective presaturation pulses 246 and a spectrally selective fat saturation pulse 248 are applied after the ECG trigger signal 249. Image data is then acquired during an acquisition window indicated at 251. A first set of peripheral views 250 are acquired during the first part of diastole in a "descending" view order in which the view most remote from the center of k-space are acquired first when motion is the greatest. This is followed by acquiring a set of central k-space samples 252 during the measured quiescent time period indicated at 254. This is followed by acquiring a second set of peripheral views 256 during the remainder of diastole. This latter set of view acquisitions 256 sample peripheral k-space in "ascending" view acquisition 256 samples k-space in ascending order such that the views most remote from the center of k-space are acquired last when coronary artery motion is greater.

By acquiring views in three separate sets 250, 252 and 256 during each cardiac cycle, the sampling of k-space can be matched to the artery motion of the patient. The scout scan identifies the quiescent period 254 during each cardiac cycle when the most important, central k-space views are acquired. The descending and ascending view orders used before and after this quiescent period enable sampling to be extended longer during each cardiac cycle because only the least affected peripheral views are acquired at the very beginning and the very end when cardiac motion is at its greatest. This enables more views to be acquired during each cardiac cycle, which in turn shortens the total scan time.

Figure 7:
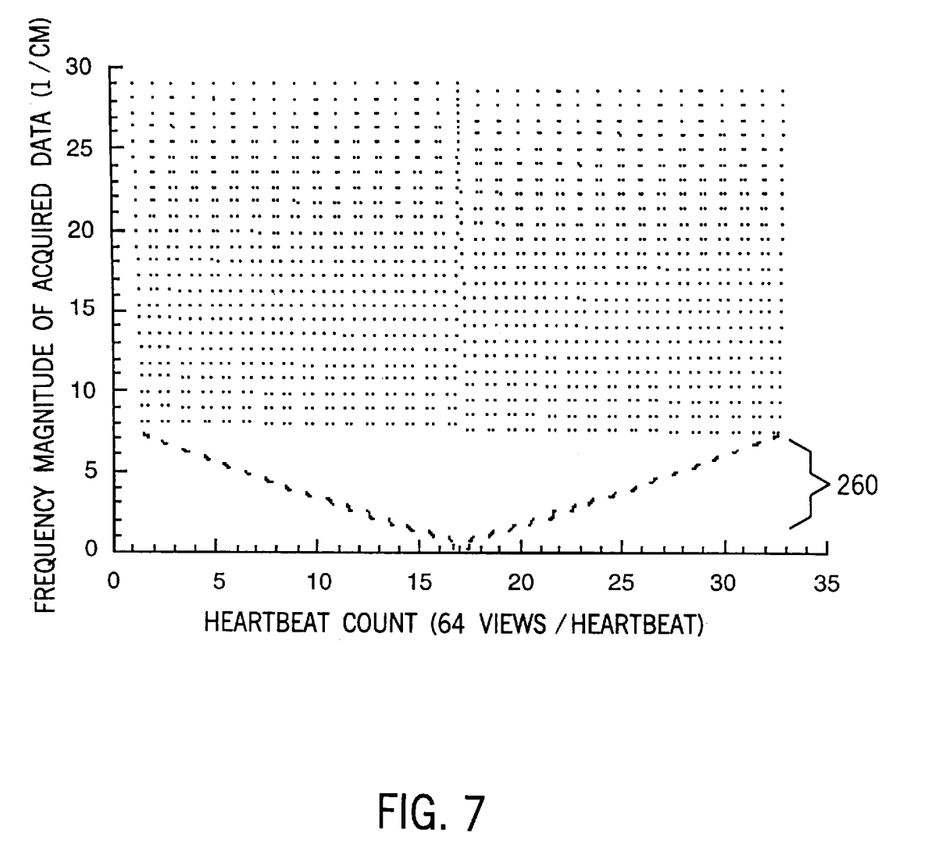
FIG. 7 is a graphic illustration of the k-space data sampling order in one exemplary 3DFT scan according to the present invention.

FIG. 7 illustrates one embodiment of how k-space is sampled during a 3D acquisition of a 256 by 128 by 16 element k-space data matrix. The vertical axis indicates the distance of the k-space sample from the center of k-space and the horizontal axis indicates the cardiac cycle number, or heartbeat count. This scan is completed in 32 cardiac cycles, with one-quarter of the central most views indicated at 260 being acquired during the quiescent periods 254 of the cardiac cycles. In the particular scan illustrated in FIG. 7, sixteen central views are acquired during an 80 msec quiescent period 254 of each cardiac cycle, twenty-four peripheral views are acquired in descending order at the beginning 250 of each acquisition window 251 in 120 msecs, and twenty-four peripheral views are acquired in ascending order in 120 msecs at the end 256 of each acquisition window 251.

There are many possible view orders which may be employed to practice the present invention. The movement of the subject arteries during the cardiac acquisition window may be divided into a plurality of time segments, and these time segments may be mapped to different segments of k-space. During the subsequent scan, each k-space segment is sampled during its corresponding time segment.

Figure 8:
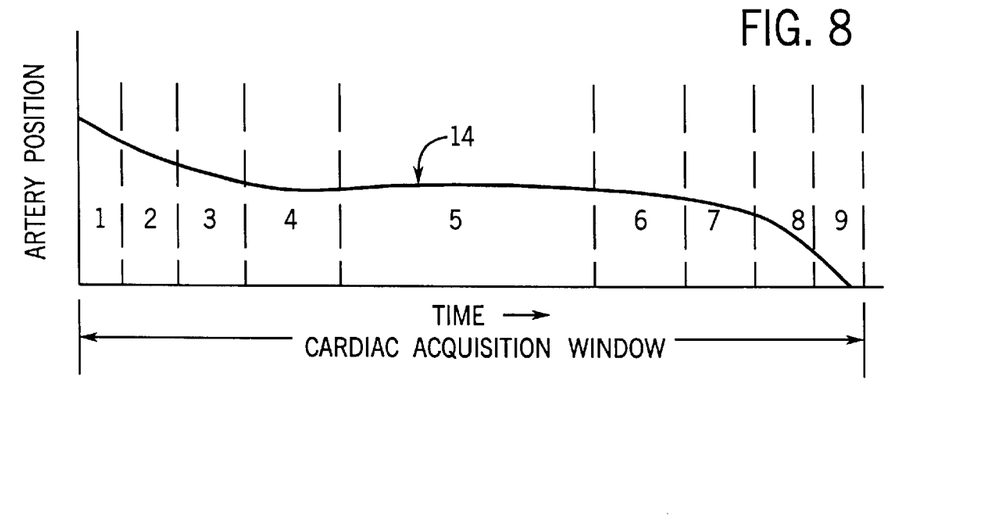
FIG. 8 is an exemplary graph showing arterial motion during a cardiac acquisition window.

Referring particularly to FIG. 8, the artery position measurements made during an exemplary scout scan are plotted as a function of time during the cardiac acquisition window to form curve 14. This time window during which NMR data is acquired during each cardiac cycle is divided into nine time segments 1–9, where time segment 5 corresponds to the quiescent time period 254 discussed above. These time regions 1–9 may be mapped to specific regions of k-space and used to produce tables which are used in the subsequent scan.

Figure 9:
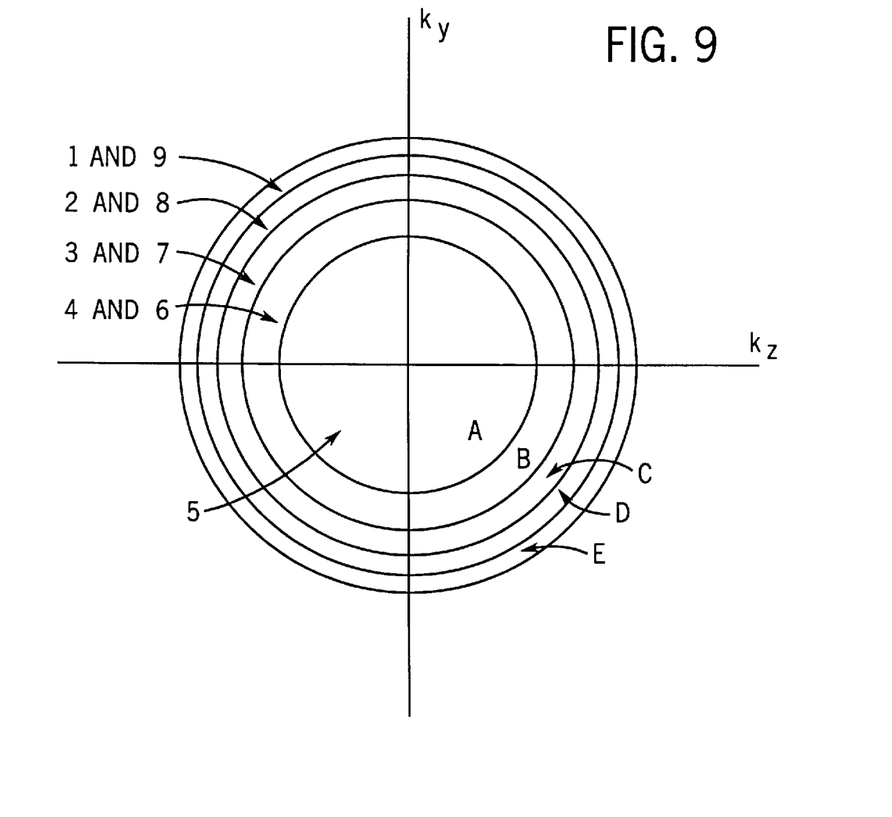
FIG. 9 is a graphic representation of one method for dividing up k-space into separate regions or segments.

Referring to FIG. 9, the time segments 1–9 may, for example, be mapped to k-space regions A–E. The k-space segmentation in this example is comprised of a central region A centered on the origin of k-space and four annular, concentric peripheral regions B–E. The data acquisition time segments 1–9 are mapped as shown, with the quiescent time segment 5 mapped to the central k-space region A. This sampling strategy corresponds to that illustrated in FIG. 7 and discussed above.

Figure 10:
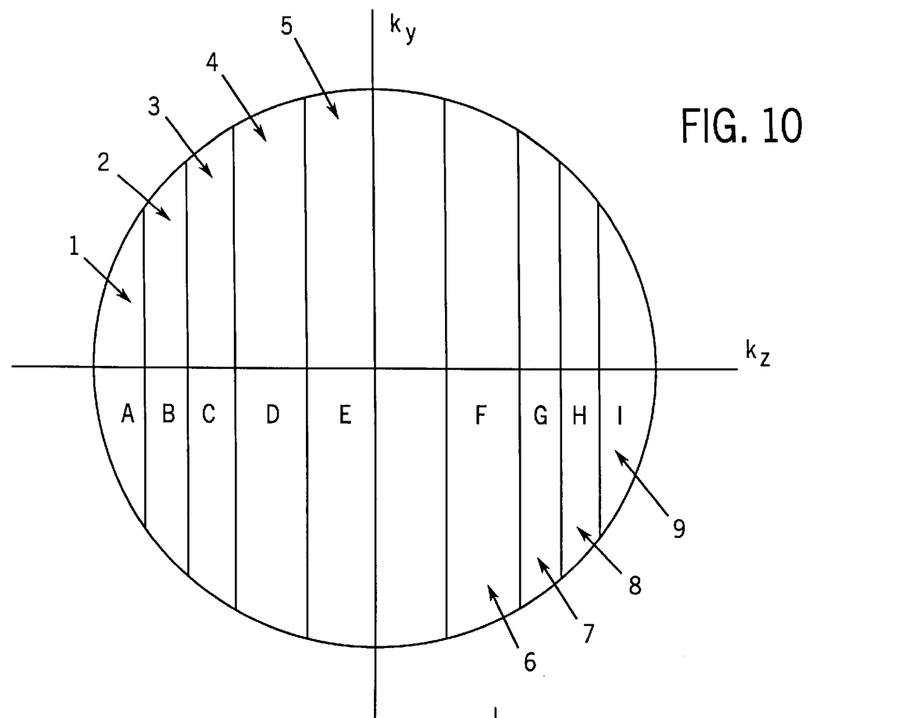
FIG. 10 is a graphic representation of another method for dividing up k-space into separate regions or segments.
Figure 11:
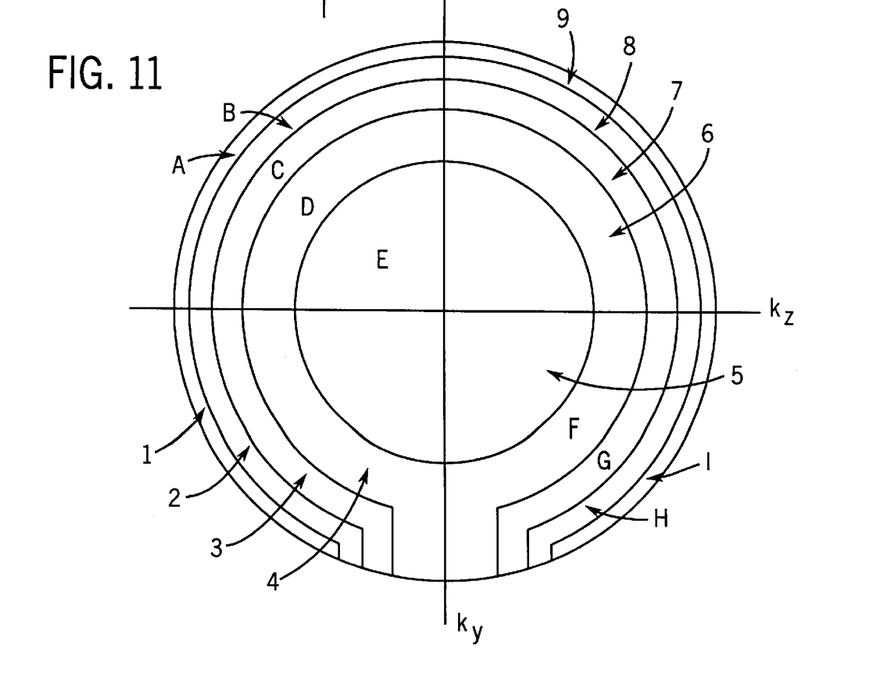
FIG. 11 is a graphic representation of yet another method for dividing up k-space into separate regions or segments.

Referring particularly to FIGS. 10 and 11, other sampling strategies may be used to smooth motion over the k-space acquisition. In FIG. 10, the nine acquisition time segments 1–9 are mapped to nine k-space regions A–I as shown. Within each k-space region A–I, the sampling is sequential along the $k_z$ axis and the sampling is edge-center-edge along the $k_y$ axis. The sampling method in FIG. 10 is particularly valuable for non-cartesian acquisition, such as a spiral acquisition. In spiral acquisition, ky corresponds to the spiral interleaf index. The zero motion along "ky" in FIG. 10 minimizes artifacts in each spiral disk of a 3D volume stack.

Another optimal, edge-center-edge sampling order is depicted in FIG. 11. This sampling order combines the benefits of zero motion at a circular region E to which the quiescent time segment 5 is mapped along with a smooth motion distribution across k-space. Therefore, this method is advantageous for data acquisitions such as the widely used Cartesian Fourier acquisition. A variation of the method in FIG. 11 is to replace the contour lines with saddle shapes, which would allow hermitian symmetry.

Figure 12:
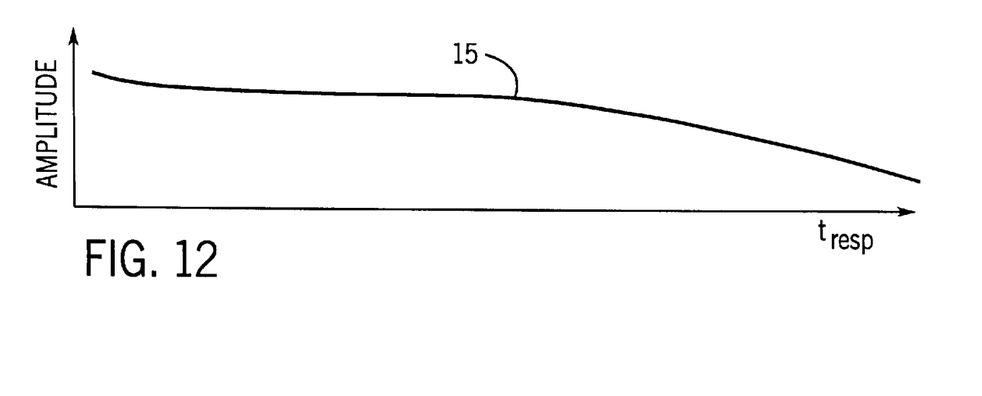
FIG. 12 is an exemplary graph showing respiratory motion during a respiratory gating window.

As indicated above, the present invention can also be used to tailor the sampling of k-space during an MRI scan for respiratory motion. As with the cardiac method described above, navigator echoes can be acquired continuously throughout the respiratory cycle. Positions of the heart or the diaphragm can be detected from the navigator echoes, generating a respiratory histogram. As shown in FIG. 12, the sorted respiratory graph 15 consists of points in the respiratory gating window sorted sequentially according to the motion amplitude. Here the respiratory amplitude is the SI displacement.

The number of points in the graph 15 is the required number of heartbeats to acquire all the image data (number of phase encodes divided by the number of echoes acquired per heartbeat). The duration (repetition) at each amplitude is proportional to the probability in the histogram. In this manner, the horizontal axis in FIG. 12 has the dimension of time, and is referred to as the pseudo respiratory time $t_{resp}$. The sorted respiratory motion graph 15 is similar to the cardiac motion graph 14 in FIG. 8, and view orders illustrated in FIGS. 9–11 can be used directly for respiratory view ordering by dividing the respiratory gating window into time segments and mapping them to corresponding regions of k-space.

The present invention may also be employed to address both cardiac motion and respiratory motion simultaneously. This may be achieved with a 2D motion phase diagram shown in FIG. 13. The motion distribution on this 2D diagram is smooth and characterized by a pair of indices $(t_{card}, t_{resp})$, with $t_{card}$ corresponding to the actual time in the cardiac acquisition window, and $t_{resp}$ the pseudo respiratory time.

Figure 13:
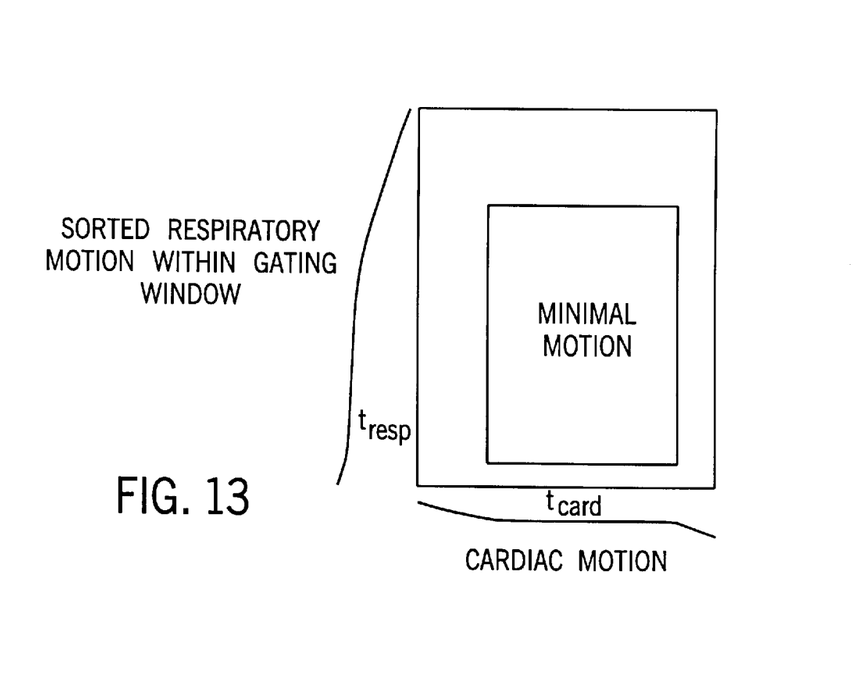
FIG. 13 is a two-dimensional motion phase diagram showing both respiratory motion and cardiac motion simultaneously.

A view order that maps the k-space center to the minimal motion area on the 2D motion phase diagram of FIG. 13 and maps other regions of k-space smoothly provides minimal motion blurring. In this manner, the above developed respiratory view ordering and cardiac view ordering are integrated to suppress both respiratory and cardiac motion effects simultaneously. The desired view order is a one-to-one mapping from the 2D motion phase diagram to the k-space to be acquired. This mapping is isometric and a homomorphism between the motion phase diagram and k-space, and there always exists such mapping.

The details of mapping from the 2D motion phase diagram to k-space, $(k_y, k_z) \Leftrightarrow (t_{card}, t_{resp})$, can be constructed in a manner similar to but generalized from that described above. The desired mapping should satisfy two conditions: 1) the center of k-space is always mapped to the area of minimal motion in the motion phase diagram; and 2) the motion distribution in k-space should be smooth. Two examples are illustrated in FIGS. 14 and 15.

Figure 14:
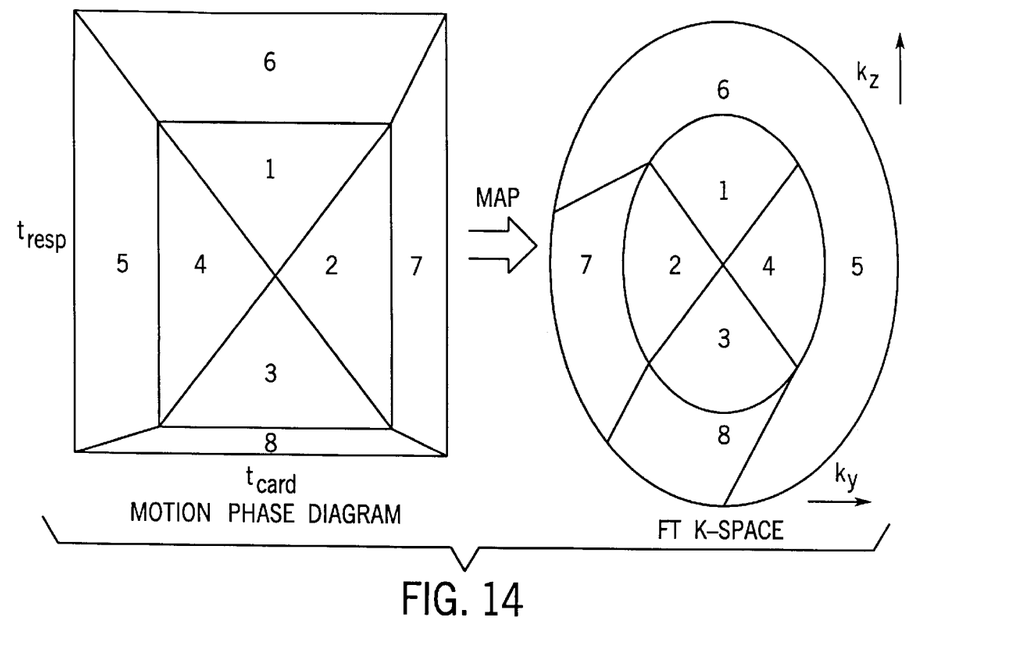
FIG. 14 is a graphic illustration showing segments of the diagram in FIG. 13 mapped to corresponding regions of k-space for one embodiment.

An exemplary view order for a Fourier transformation (FT) acquisition is illustrated in FIG. 14. The 2D motion phase diagram and the k-space to be acquired are divided into 8 segments and regions. A segment in the motion phase diagram is mapped to a k-space region marked with the same number. The exact mapping can be constructed and stored in a lookup table.

Figure 15:
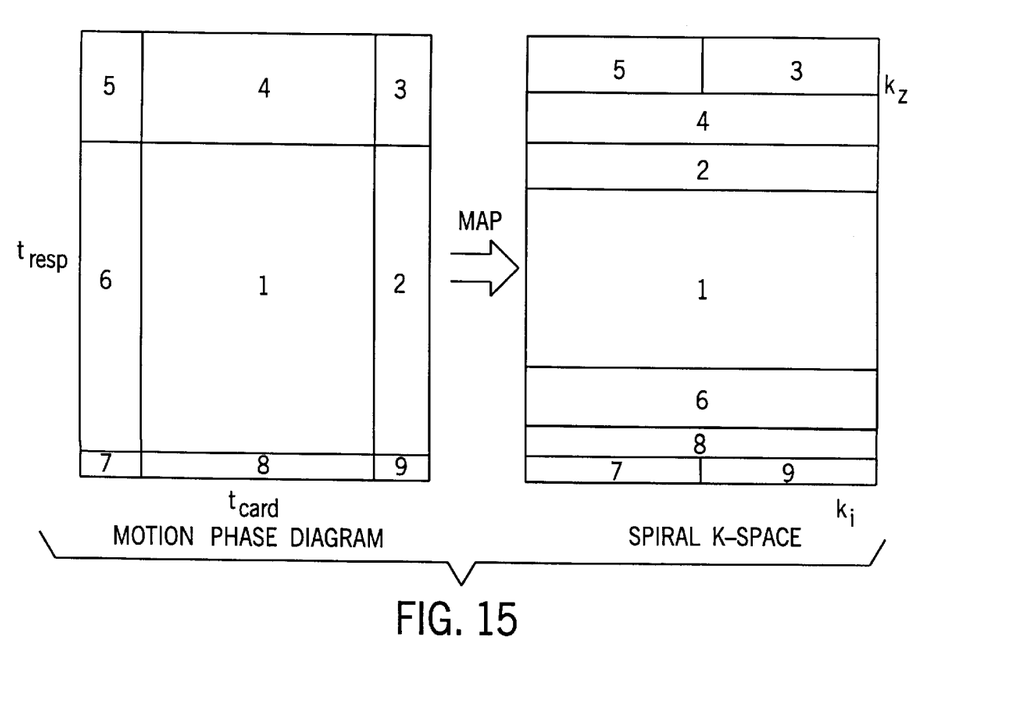
FIG. 15 is a graphic illustration showing different segments of the diagram in FIG. 13 mapped to corresponding regions of k-space in another embodiment of the invention.

The view order for a spiral acquisition is illustrated in FIG. 15. The motion phase diagram is divided into 9 segments. The spiral acquisition requires no motion along the interleave axis ($k_i$). This requirement can be easily fulfilled when there this is no motion (segment 1) or when there is only one degree of motion (segments 2, 4, 6, 8). However, the zero-$k_i$-motion requirement cannot be fulfilled when there is both cardiac and respiratory motion (segments 3, 5, 7, 9). In order to minimize motion effects, segments 3, 5, 7, 9 can be mapped to the edge of k-space, or not used at all for data acquisition (at slight increase in scan time). Asymmetry in the respiratory graph 15 (segments 4, 8) can be used to compensate asymmetry in the cardiac graph 14 (segments 6, 2) or otherwise the acquisition window or the gating window should be limited, so that the center of k-space is sampled with no motion. The positions along $k_z$ for segments 2 and 4 and segments 6 and 8 can be switched, depending the relative magnitudes of cardiac and respiratory motion.

What is claimed is:

1. A method for imaging arteries using an MRA pulse sequence in which a series of views are acquired to sample k-space, the steps comprising:

a) performing a scout scan using an NMR pulse sequence to measure movement of the arteries during a cardiac cycle;

b) identifying a quiescent period during the cardiac cycle in which the measured artery movement is minimal; and c) acquiring the views from which an image is reconstructed using the MRA pulse sequence over a succession of cardiac cycles, and arranging the view order in this acquisition such that the views which sample a central region of k-space are acquired during the quiescent periods of the cardiac cycles and views which sample peripheral regions of k-space are acquired during portions of the cardiac cycles outside the quiescent periods of the cardiac cycles.

2. The method as recited in claim 1 in which the arteries are coronary arteries and step a) is performed by:

i) performing the NMR pulse sequence repeatedly during the cardiac cycle to acquire a plurality of NMR echo signals;

ii) transforming the NMR echo signals to produce a scout image;

iii) detecting a cardiac cavity wall in the scout image; and iv) measuring the movement of the cardiac cavity wall.

3. The method as recited in claim 1 in which the view order is arranged such that views which sample a peripheral region of k-space are acquired for a time period prior to the quiescent period in each of the succession of cardiac cycles.

4. The method as recited in claim 3 in which the view order is arranged such that views which sample the peripheral region of k-space are also acquired for a time period after the quiescent period in each of the succession of cardiac cycles.

5. The method as recited in claim 3 in which the peripheral views acquired prior to each quiescent period are acquired in descending view order.

6. The method as recited in claim 4 in which the peripheral views acquired after each quiescent period are acquired in ascending view order.

7. A method for imaging patient arteries with an MRI system using an MRA pulse sequence in which a series of views are acquired to sample k-space, the steps comprising:

a) performing a scout scan using an NMR pulse sequence to measure movement of the arteries during an acquisition window;

b) dividing the acquisition window into a plurality of time segments including a quiescent time segment during which there is minimal arterial motion;

c) producing a view order table by mapping each time segment to a corresponding region of k-space to be sampled and wherein the quiescent time segment is mapped to a central region of k-space and another time segment is mapped to a peripheral region of k-space;

d) acquiring image data using the MRA pulse sequence during a series of acquisition windows, wherein each region of k-space is sampled during its corresponding time segment in each acquisition window.

8. The method as recited in claim 7 in which the acquisition window occurs at a selected time during the patient's cardiac cycle.

9. The method as recited in claim 7 in which the acquisition window occurs at a selected time during the patient's respiratory cycle.

10. The method as recited in claim 7 in which the movement is produced by respiratory motion and the acquisition window occurs during a gating window during each respiratory cycle of the patient.

11. The method as recited in claim 10 which includes:

performing a second scout scan to measure movement of the arteries during a cardiac acquisition window;

dividing the cardiac acquisition window into a plurality of cardiac time segments including a cardiac quiescent time segment during which there is minimal arterial motion; and wherein the view order table produced in step c) includes mapping the cardiac time segments to corresponding regions of k-space.

* * * * *